US010197782B2

(12) United States Patent
Kataoka et al.

(10) Patent No.: US 10,197,782 B2
(45) Date of Patent: Feb. 5, 2019

(54) LIGHT MEASUREMENT DEVICE, LIGHT MEASUREMENT METHOD, AND LIGHT MEASUREMENT PROGRAM

(75) Inventors: Takuji Kataoka, Hamamatsu (JP); Masanori Matsubara, Hamamatsu (JP)

(73) Assignee: HAMAMATSU PHOTONICS K.K., Hamamatsu-shi, Shizuoka (JP)

(*) Notice: Subject to any disclaimer, the term of this patent is extended or adjusted under 35 U.S.C. 154(b) by 222 days.

(21) Appl. No.: 14/127,700

(22) PCT Filed: Jun. 19, 2012

(86) PCT No.: PCT/JP2012/065667
§ 371 (c)(1),
(2), (4) Date: Feb. 12, 2014

(87) PCT Pub. No.: WO2012/176783
PCT Pub. Date: Dec. 27, 2012

(65) Prior Publication Data
US 2014/0152799 A1  Jun. 5, 2014

(30) Foreign Application Priority Data
Jun. 21, 2011  (JP) .................. 2011-137315

(51) Int. Cl.
H04N 7/18 (2006.01)
G02B 21/36 (2006.01)
(Continued)

(52) U.S. Cl.
CPC ......... *G02B 21/365* (2013.01); *G06K 9/0014* (2013.01); *G06T 7/0016* (2013.01);
(Continued)

(58) Field of Classification Search
CPC ......... G06T 7/0016; G06T 2207/10016; G06T 2207/10056; G06T 2207/30024;
(Continued)

(56) References Cited

U.S. PATENT DOCUMENTS 5,047,846 A   9/1991  Uchiyama et al.
6,462,771 B1  10/2002 Kitagawa
(Continued)

FOREIGN PATENT DOCUMENTS

CN   1690696    11/2005
CN  101712926    5/2010
(Continued)

OTHER PUBLICATIONS

Ross, James, "Microstimulation and Multicellular Analysis: A Neural Interfacing System for Spatiotemporal Stimulation," In: "PHD Thesis", Institute of Technology, Department of Biological Engineering, Georgia Institute of Technology, Aug. 1, 2008, pp. 1-151.
(Continued)

Primary Examiner — Y Lee
Assistant Examiner — Richard B Carter
(74) Attorney, Agent, or Firm — Drinker Biddle & Reath LLP

(57) ABSTRACT

The light measurement device is provided with a moving-image acquisition part and an analysis processing part. The analysis processing part includes: a luminance-value-data acquisition part for acquiring the luminance value data; a luminance-value extraction part for extracting a peak value and a bottom value of the luminance value, from the luminance value data; a pixel extraction part for extracting a target pixel configuring an image of a predetermined cell from a plurality of pixels, on the basis of the evaluation value. The pixel extraction part extracts, as the evaluation value, the target pixel on the basis of at least one of an amplitude of the luminance value obtained from a difference between the peak value and the bottom value and a change ratio of the luminance value obtained from a ratio of the peak value relative to the bottom value.

18 Claims, 10 Drawing Sheets

(51) Int. Cl.
*G06T 7/00* (2017.01)
*G06K 9/00* (2006.01)
*G01N 21/64* (2006.01)

(52) U.S. Cl.
CPC ..... *G01N 21/6452* (2013.01); *G01N 21/6458* (2013.01); *G06T 2207/10016* (2013.01); *G06T 2207/10056* (2013.01); *G06T 2207/30024* (2013.01); *G06T 2207/30072* (2013.01)

(58) Field of Classification Search
CPC ........ G06T 2207/30072; G06K 9/0014; G02B 21/365; G01N 21/6452; G01N 21/6458
USPC .............................. 348/79; 359/368; 382/382
See application file for complete search history.

(56) References Cited

U.S. PATENT DOCUMENTS

| | | | |
|---|---|---|---|
| 2004/0241832 | A1 | 12/2004 | Muraki et al. |
| 2006/0018013 | A1* | 1/2006 | Suzuki ............... G01N 21/6452 359/368 |
| 2007/0059763 | A1 | 3/2007 | Okano et al. |
| 2008/0056610 | A1* | 3/2008 | Kanda .................. G02B 21/365 382/282 |
| 2009/0141960 | A1* | 6/2009 | Yamamoto ......... G01N 21/6458 382/133 |
| 2010/0253774 | A1* | 10/2010 | Yoshioka ............... G02B 21/16 348/79 |
| 2010/0295932 | A1* | 11/2010 | Yokomachi ............. G06T 5/008 348/79 |
| 2010/0322906 | A1 | 12/2010 | Matsuyama et al. |
| 2011/0135171 | A1* | 6/2011 | Galigekere ........... G06T 7/0012 382/128 |
| 2011/0266074 | A1 | 11/2011 | Fan et al. |
| 2011/0310239 | A1* | 12/2011 | Ogihara ................. H04N 5/243 348/79 |
| 2013/0322688 | A1 | 12/2013 | Tsuchiya et al. |
| 2014/0152798 | A1* | 6/2014 | Kataoka ............. G01N 21/6452 348/79 |
| 2014/0152799 | A1 | 6/2014 | Kataoka et al. |

FOREIGN PATENT DOCUMENTS

| | | |
|---|---|---|
| CN | 101782524 | 7/2010 |
| JP | S63-233392 A | 9/1988 |
| JP | 2000-275529 | 10/2000 |
| JP | 2000-275539 A | 10/2000 |
| JP | 2003-014737 A | 1/2003 |
| JP | 2005-027623 A | 2/2005 |
| JP | 2005-102629 | 4/2005 |
| JP | 2005-291720 | 10/2005 |
| JP | 2006-200987 A | 8/2006 |
| JP | 2006-340686 | 12/2006 |
| JP | 2007-121106 A | 5/2007 |
| JP | 2007-278984 | 10/2007 |
| JP | 2007-278985 A | 10/2007 |
| JP | 5869239 B2 | 2/2016 |
| WO | WO 2007/013551 | 2/2007 |
| WO | WO 2010/143420 | 12/2010 |

OTHER PUBLICATIONS

Holthoff, Knut, et al., "Rapid Time Course of Action Potentials in Spines and Remote Dendrites of Mouse Visual Cortex Neurons," The Journal of Physiology, vol. 588, No. 7, Mar. 30, 2010, pp. 1085-1096.
U.S. Office Action dated Nov. 30, 2015 that issued in U.S. Appl. No. 14/127,669 including Double Patenting Rejections on pp. 3-6.
Office Action dated Sep. 8, 2016 in U.S. Appl. No. 14/127,669.
Office Action dated Feb. 21, 2017 in U.S. Appl. No. 14/127,669 with a double-patenting rejection on p. 3.
U.S. Office Action dated Aug. 23, 2017 that issued in U.S. Appl. No. 14/127,669 including Double Patenting Rejections on pp. 2-6.
Office Action dated Mar. 21, 2018 in U.S. Appl. No. 14/127,669.

* cited by examiner

LIGHT MEASUREMENT DEVICE, LIGHT MEASUREMENT METHOD, AND LIGHT MEASUREMENT PROGRAM

TECHNICAL FIELD

The present invention relates to a light measurement device for measuring light emitted from a cell, a light measurement method, and a light measurement program.

BACKGROUND ART

In the drug development field, there is a case where an influence of a drug administered to a sample such as a cell is evaluated by measuring light emitted from the cell. Patent Literature 1 discloses a method for evaluating a cell by performing image processing on a cell image of animals and plants. In this method, a protrusion protruded outward from a cell main body such as a nerve cell is extracted from a cell image by an image processing technique. In this image processing technique, a pixel having a luminance value that exceeds a predetermined threshold value is extracted as a subject to be analyzed from a plurality of pixels configuring an image.

CITATION LIST

Patent Literature

Patent Literature 1: Japanese Patent Application Laid-Open No. 2003-14737

SUMMARY OF INVENTION

Technical Problem

Generally, depending on each type of cell, temporal emission characteristics of light may differ. For example, a reaction of a nerve cell is characterized in a temporal change. Further, there is a case where an image including light emitted from a specific cell such as a stained cell includes a pixel which receives light having a fixed luminance value and a pixel which receives light having a luminance value that temporally alters. However, in the image processing technique described in Patent Literature 1, it is not possible to distinguish a cell image from which light having a fixed luminance value is emitted and a cell image from which light having a luminance value that temporally alters is emitted. Further, in the image processing technique described in Patent Literature 1, it is not possible to distinguish a plurality of types of cell images having different temporal emission characteristics of light.

In view of the above-described problem, it is an object of the present invention to provide a light measurement device with which it is possible to divide an image of a cell having a temporally altering luminance value in an image including light emitted from a sample including a cell such as a nerve cell, a light measurement method t, and a light measurement program.

Solution to Problem

A light measurement device according to one aspect of the present invention is a light measurement device for measuring light emitted from a cell held by a sample case having a holding part for holding a sample including the cell. The device is provided with: a moving-image acquisition means for acquiring moving image data of a two-dimensional light image by detecting a two-dimensional light image of a sample case including light emitted from a sample held inside a holding part of the sample case; and an analysis processing means for performing analysis processing on the moving image data. The analysis processing means includes: a luminance-value-data acquisition means for acquiring the luminance value data indicating a temporal alteration in a luminance value in a plurality of pixels configuring a region corresponding to the holding part from a region corresponding to a holding part included in the moving image data; a luminance-value extraction means for extracting a peak value and a bottom value of luminance value from the luminance value data; and a pixel extraction means for calculating, on the basis of the peak value and the bottom value, an evaluation value for evaluating the temporal alteration in the luminance value and extracting a target pixel configuring an image of a predetermined cell from a plurality of pixels on the basis of the evaluation value. The pixel extraction means extracts the target pixel on the basis of at least one of, as the evaluation value, an amplitude of the luminance value obtained from a difference between the peak value and the bottom value and a change ratio of the luminance value obtained from a ratio of the peak value relative to the bottom value.

A light measurement method according to one aspect of the present invention is a light measurement method for measuring light emitted from a cell held by a sample case having a holding part for holding a sample including the cell. The method comprises: a moving-image acquisition step of acquiring moving image data of a two-dimensional light image by detecting a two-dimensional light image, of a sample case, including light emitted from the sample held inside the holding part of a sample case; and an analysis processing step of performing analysis processing on the moving image data. The analysis processing step includes: a luminance-value-data acquisition step of acquiring luminance value data indicating a temporal alteration in a luminance value in a plurality of pixels configuring a region corresponding to the holding part, from a region corresponding to a holding part included in the moving image data; a luminance-value extraction step of extracting a peak value and a bottom value of a luminance value from the luminance value data; and a pixel extraction step of calculating, on the basis of the peak value and the bottom value, an evaluation value for evaluating the temporal alteration in the luminance value and extracting a target pixel configuring an image of a cell from a plurality of pixels on the basis of the evaluation value. The pixel extraction step extracts, as the evaluation value, the target pixel on the basis of at least one of an amplitude of the luminance value obtained from a difference between the peak value and the bottom value and a change ratio of the luminance value obtained from a ratio of the peak value relative to the bottom value.

A light measurement program according to one aspect of the present invention is a light measurement program for measuring light emitted from a cell held by a sample case having a holding part for holding a sample including the cell. The program causes a computer to function, a luminance-value-data acquisition means for acquiring luminance value data indicating the temporal alteration in a luminance value in a plurality of pixels configuring a region corresponding to a holding part, from a region corresponding to a holding part included in the moving image data, relative to moving image data which is acquired by a moving-image acquisition means and in which a two-dimensional light image of a sample case including the light emitted from a sample held inside a holding part of the sample case is detected; a luminance-value extraction means for extracting a peak value and a bottom value of a luminance value from the luminance value data; and a pixel extraction means for calculating, on the basis of the peak value and the bottom value, an evaluation value for evaluating the temporal alteration in the luminance value and extracting a target pixel configuring an image of a predetermined cell from a plurality of pixels on the basis of the evaluation value. The pixel extraction means has a function of extracting, as the evaluation value, the target pixel on the basis of at least one of an amplitude of the luminance value obtained from a difference between the peak value and the bottom value and a change ratio of the luminance value obtained from a ratio of the peak value relative to the bottom value.

According to the light measurement device, the light measurement method, or the light measurement program, a two-dimensional light image of a sample case including light emitted from a sample including the cell held inside a holding part of the sample case is detected, and two-dimensional moving image data is acquired. Then, luminance value data indicating temporal alteration in a luminance value in a plurality of pixels configuring the moving image data is acquired. Next, a peak value and a bottom value of the luminance value are acquired from the luminance value data. On the basis of either one of an amplitude of the luminance value obtained from a difference between the peak value and the bottom value or a change ratio of the luminance value obtained from a ratio of the peak value relative to the bottom value, a target pixel configuring an image of a predetermined cell is extracted from a plurality of pixels. Thus, according to the light measurement device, the light measurement method, or the light measurement program, a target pixel is extracted on the basis of the luminance value data, and it is therefore possible to divide a target pixel configuring an image of a predetermined cell from which light having a luminance value that temporally alters is emitted.

In a light measurement device according to one aspect of the present invention, the pixel extraction means may further extract, as the evaluation value, a target pixel on the basis of at least one of: a peak cycle; a peak count; a peak time defined by a time until the luminance value reaches from a predetermined timing to a peak; a rising time defined by a time until the luminance value reaches the peak value from the bottom value; a falling time defined by a time until the luminance value returns from the peak value to the bottom value; and a peak amplitude range that is a difference between the peak time in one pixel and the peak time in another pixel adjacent to the one pixel. According thereto, the light measurement device uses, as a parameter for extracting the target pixel, the peak cycle, the peak count, the peak time, the rising time, the falling time and the peak amplitude range. Therefore, it is possible to minutely distinguish the characteristics of the temporal alteration in the luminance value, so that it is possible to accurately divide the target pixel configuring the image of a predetermined cell.

In the light measurement device according to one aspect of the present invention, the analysis processing means may further include: a correction means for correcting a phase deviation between the plurality of luminance value data by calculating corrected luminance value data in which the phase has been corrected; and a processing means for processing the plurality of corrected luminance value data by calculating averaged luminance value data that is an average of the plurality of corrected luminance value data. According thereto, the correction means calculates the corrected luminance value data by correcting the luminance value data of the pixel selected by the pixel extraction part. Then, the processing means averages a plurality of corrected luminance value data by calculating the averaged luminance value data. Therefore, it is possible to perform analysis processing in which measurement sensitivity to the light emitted from the cell is improved.

In the light measurement device according to one aspect of the present invention, the analysis processing means may further include: an identification means for identifying an image configured by the target pixel by comparing the averaged luminance value data and specimen luminance value data acquired in advance. According thereto, it is possible to distinguish a type of an image configured by a desired cell image.

A light measurement device according to one aspect of the present invention is a light measurement device for measuring light emitted from a cell held by a sample case having a holding part for holding a sample including the cell. The device is provided with: a moving-image acquisition means for acquiring moving image data of a two-dimensional light image by detecting a two-dimensional light image of the sample case including light emitted from a sample held inside a holding part of the sample case; and an analysis processing means for performing analysis processing on the moving image data. The analysis processing means includes: a luminance-value-data acquisition means for acquiring luminance value data indicating the temporal alteration in a luminance value in a plurality of pixels configuring a region corresponding to a holding part, from a region corresponding to a holding part included in the moving image data; a pixel extraction means for calculating, on the basis of a feature value indicating the waveform of the luminance value data, an evaluation value for evaluating the temporal alteration in the luminance value and extracting a target pixel configuring an image of a predetermined cell from a plurality of pixels on the basis of the evaluation value; and a data processing part for performing predetermined processing on the luminance value data in the target pixel.

Advantageous Effects of Invention

According to the light measurement device, the light measurement method and the light measurement program of the present invention, it is possible to divide a pixel configuring an image of a cell in which a luminance value temporally alters in an image including light emitted from a sample including a nerve cell, for example.

DESCRIPTION OF EMBODIMENTS

Hereinafter, with reference to the attached drawings, an embodiment of a light measurement device, a light measurement method, and a light measurement program will be described in detail. It should be noted that in the description of the drawings, the same reference sign is given to the same element, and duplicate explanations are omitted.

Figure 1:
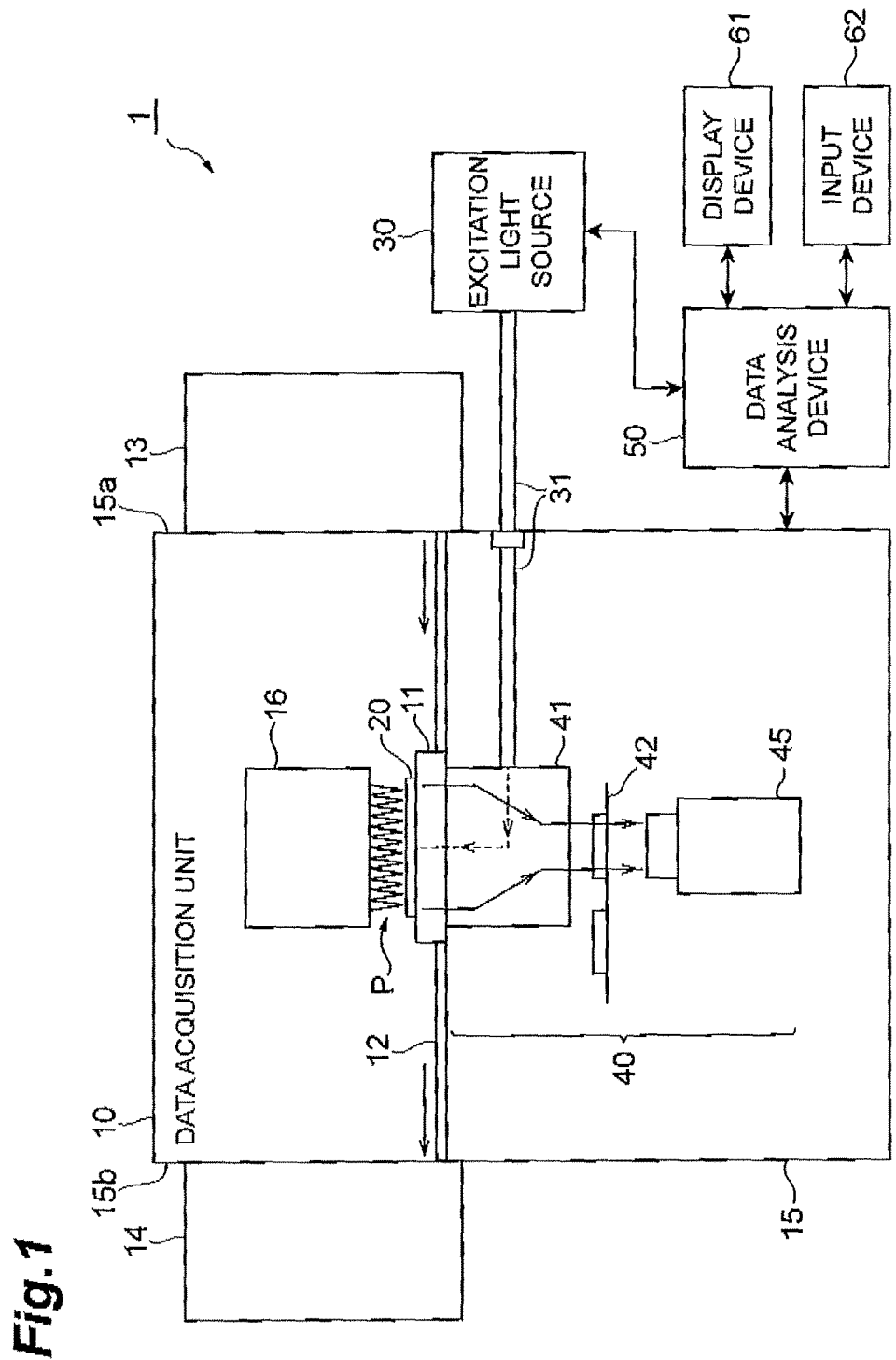
FIG. 1 is a diagram schematically showing one embodiment of a light measurement device.
Figure 2:
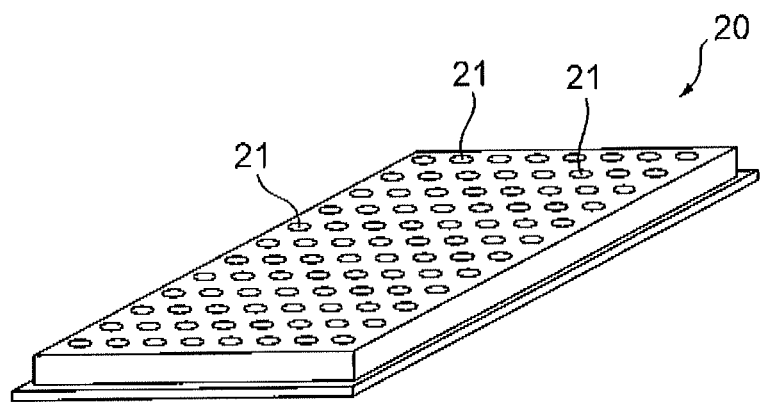
FIG. 2 is a diagram showing one example of the configuration of a micro plate.
Figure 3:
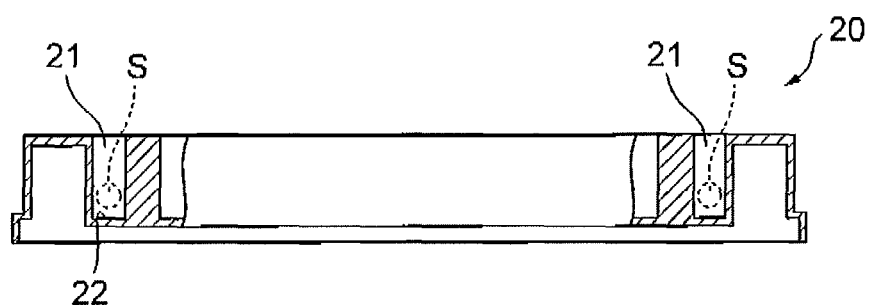
FIG. 3 is a diagram showing a sectional structure obtained when the micro plate shown in FIG. 2 is viewed laterally.

FIG. 1 is a diagram schematically showing the configuration of one embodiment of a light measurement device 1. FIG. 2 is a diagram showing one example of the configuration of a micro plate. FIG. 3 is a diagram showing a sectional structure obtained when the micro plate shown in FIG. 2 is viewed laterally. In the light measurement device 1, a micro plate 20 may be used as one example of a sample case. The light measurement device 1 is a device for measuring a fluorescence from a sample S that is held by the micro plate 20 and arranged at a measurement position P (see FIG. 3).

The sample S includes a predetermined cell. Examples of the predetermined cell include a nerve cell. Further, the light measurement device, the light measurement method, and the light measurement program according to one embodiment can generally be applied not only to the fluorescence measurement but also to a light measurement where light emitted from a sample is measured such as a phosphorescence and a light emission. The configuration of the light measurement device 1 will be described below.

As shown in FIG. 1, the light measurement device 1 is configured by including a data acquisition unit 10, an excitation light source 30 and a data analysis device 50. The data acquisition unit 10 includes a black box 15 and a moving-image acquisition part 40. The black box 15 internally houses the micro plate 20 for housing therein a cell subject to fluorescence measurement. The moving-image acquisition part 40 measures the fluorescence from the sample S arranged inside the black box 15 and arranged at the measurement position P.

As shown in FIG. 2 and FIG. 3, the micro plate 20 is a planar member in which a plurality of wells (holding part) 21 are arranged in parallel in a two-dimensional array manner. Each of the plurality of wells 21 is configured so that the sample S can be held. For example, as shown in FIG. 2, as the plurality of wells 21, 8×12=96 wells 21 are arranged in a two-dimensional array manner. The shape of the well 21 may be circular or rectangular. Further, a bottom surface 22 of the micro plate 20 is formed of a material through which excitation light for fluorescence measurement entering, with irradiation, into the sample S and a fluorescence emitted from the sample S can pass. It should be noted that generally, the bottom surface 22 of the micro plate 20 provided in the light measurement device 1 may be formed of a material through which light emitted from the sample S, which is to be measured, can pass.

In the black box 15, the micro plate 20 is arranged. The micro plate 20 is held by a micro plate holder 11 having an opening for fluorescence observation. Further, in the black box 15, a micro-plate conveyance mechanism 12 is arranged. The micro-plate conveyance mechanism 12 conveys the holder 11 holding the micro plate 20 into a predetermined direction within the black box 15. The predetermined direction is a direction from the right side toward the left side in FIG. 1.

An import-side micro plate stocker 13 is arranged at one side 15a of the black box 15 which is an import side relative to the conveyance direction of the micro plate 20. The import-side micro plate stocker 13 stocks a predetermined number (for example, 25) of unmeasured micro plates 20 which holds the sample S. Further, an) export-side micro plate stocker 14 is arranged at the other side 15b of the black box 15 which is an export side relative to the conveyance direction of the micro plate 20. The export-side micro plate stocker 14 stocks the measured micro plate 20.

In such a configuration, the micro plate 20 imported from the import-side micro plate stocker 13 into the black box 15 is held by the micro plate holder 11 and conveyed by the conveyance mechanism 12. Then, the micro plate 20 is once stopped at the measurement position P, and in this state, the required light measurement is performed on the sample S held by the micro plate 20. After the measurement has been completed, the micro plate 20 is again conveyed by the conveyance mechanism 12, and exported to the export-side micro plate stocker 14. It should be noted that in FIG. 1, a specific configuration illustration of the conveyance mechanism 12 for importing, conveying and exporting the micro plate 20 and the stockers 13 and 14 is omitted.

A dispensing device 16 is arranged above the measurement position P. The dispensing device 16 dispenses a reagent, etc., into the well 21 of the micro plate 20. The measurement position P is a position at which the micro plate 20 and the sample S held thereby are arranged when the fluorescence measurement is executed. The moving-image acquisition part 40 is arranged below the measurement position P. The moving-image acquisition part 40 detects the fluorescence emitted via the bottom surface 22 of the micro plate 20 from the sample S housed in the well 21.

The moving-image acquisition part 40 is a moving-image acquisition means for acquiring moving image data of a two-dimensional light image. The moving-image acquisition part 40 detects a two-dimensional light image including a light image from the plurality of wells 21 of the micro plate 20. The two-dimensional light image includes the light emitted from the sample S held in the well 21 of the micro plate 20. In the present embodiment, the moving-image acquisition part 40 has a two-dimensional pixel structure in which a plurality of pixels are two-dimensionally arrayed, and has an image pickup device 45 capable of acquiring a fluorescence image which is a two-dimensional light detection image by the fluorescence emitted from the sample S. For the image pickup device 45, for example, a highly sensitive CCD camera or a CMOS image camera may be used. Further, where necessary, the moving-image acquisition part 40 may include an image amplifying tube, a relay lens, etc., arranged before the image pickup device 45.

A light-guide optical system 41 is arranged between the measurement position P at which the micro plate 20 is arranged and the image pickup device 45. The light-guide optical system 41 is an optical system for guiding the two-dimensional light image acquired when the micro plate 20 is viewed from the bottom surface 22 side, toward the image pickup device 45. In the micro plate 20, the sample S is held in each of the plurality of wells 21. It is possible to appropriately configure the light-guide optical system 41 by an optical element capable of realizing a required function (for example, a light condensing function, a light-imagereduction function, etc.) according to a configuration, etc., of the micro plate 20 and the image pickup device 45. For such a light-guide optical system 41, an optical element having an optical reduction function of imparting a resolution where there is at least one pixel per one cell may suffice. For example, a taper fiber may be adopted (see Japanese Patent Application Laid-Open No. 2001-188044).

An optical filter part 42 is arranged between the light-guide optical system 41 and the image pickup device 45. The optical filter part 42 arranges, converts, etc., the optical filter onto a light guide path of the fluorescence, where necessary. However, when such an optical filter part 42 is not necessary, the optical filter part 42 may be omitted.

The light measurement device 1 includes an excitation light source 30. The excitation light source 30 is an excitation-light supply means for supplying the sample S with excitation light for fluorescence measurement. It is possible to appropriately configure the excitation light source 30 according to types of the sample S subject to the fluorescence measurement, a wavelength of the excitation light entering, with irradiation, the sample S, etc. It is possible to configure the excitation light source 30 by an illumination light source for supplying light, and an optical filter part for selecting or switching the wavelength of the excitation light, for example. Further, when it is not necessary to supply the excitation light depending on types of light measurement performed on the sample S, the light measurement device 1 may be configured so that the excitation light source 30 is not arranged.

As shown in FIG. 1, the excitation light source 30 is arranged outside the black box 15 and connected to the light-guide optical system 41 via an excitation-light-supplying light guide 31. The excitation light supplied from, the excitation light source 30 enters, with irradiation, the sample S via the excitation-light-supplying light guide 31 and the light-guide optical system 41. With such a configuration, the light-guide optical system 41 is an optical system capable of guiding the two-dimensional light image from the micro plate 20 and the sample S to the image pickup device 45, and guiding the excitation light from the excitation light source 30 to the sample S. Such an optical system can be configured by using a dichroic mirror, etc., for passing the fluorescence from the micro plate 20 and reflecting the excitation light from the excitation light source 30, for example. It should be noted that in FIG. 1, optical paths of the fluorescence and the excitation light in the light-guide optical system 41 are schematically shown by using a solid line and a dotted line, respectively.

The light measurement device 1 includes a data analysis device 50. The data analysis device 50 is an analysis processing means for performing analysis processing on the moving image data including the light detection image acquired by the moving-image acquisition part 40. The data analysis device 50 controls an operation of each part of the data acquisition unit 10 and the excitation light source 30 so as to control a fluorescence measurement on the sample S in the light measurement device 1. To the data analysis device 50, a display device 61 for displaying measurement results, etc., and an input device 62 used for data input, input of a necessary instruction for the fluorescence measurement, etc., are connected.

With the above-described configuration, the excitation light for fluorescence measurement enters, with irradiation, the sample S. The excitation light is supplied from the excitation light source 30 via the light guide 31 and the light-guide optical system 41. The sample S is held inside the well 21 of the micro plate 20 and arranged at the measurement position P within the black box 15. Then, the two-dimensional light image including the fluorescence emitted from the sample S is guided to the image pickup device 45 via the light-guide optical system 41, and moving image data of the two-dimensional light image is acquired at a predetermined frame rate by the image pickup device 45. The moving image data including the fluorescence image acquired by the moving-image acquisition part 40 is sent to the data analysis device 50. Then, the data analysis device 50 extracts a target pixel configuring an image of a nerve cell from the input moving image data and performs analysis processing necessary for evaluation, etc.

It should be noted that the sample case is not limited to the above-described micro plate. The plurality of samples S may be held in a dish such as a petri dish as the sample case. The light measurement device 1 may be configured as a device for observing a sample held in the petri dish via a microscope.

Figure 4:
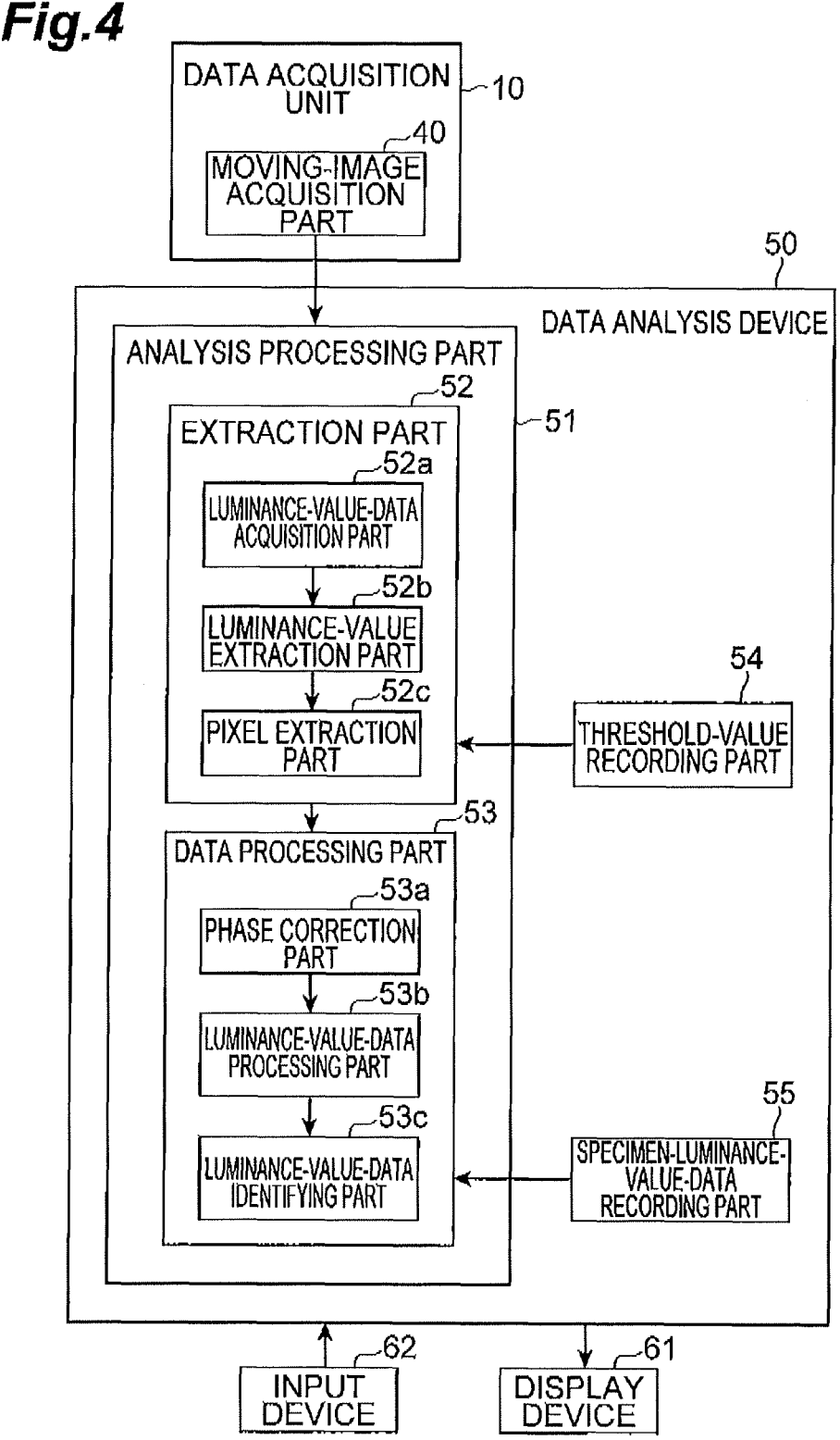
FIG. 4 is a diagram showing one example of the configuration of a data analysis device.

FIG. 4 is a diagram showing one example of the configuration of the data analysis device provided in the light measurement device 1 according to one embodiment.

The data analysis device 50 is an information processing device for acquiring the luminance value data for each pixel from the moving image data, extracting the target pixel configuring the image of the nerve cell to be analyzed on the basis of the luminance value data, and executing predetermined analysis processing on the target pixel. The moving image data is obtained by converting the image obtained by photographing the micro plate 20 including the light radiated from the sample S held within the above-described well 21, into digital data. The moving image data may be input to the data analysis device 50 via a communication network or a recording medium such as a CD-ROM, a DVD or a semiconductor memory.

The data analysis device 50 is provided with an analysis processing part 51, a threshold-value recording part 54 and a specimen-luminance-value-data recording part 55, as a functional constituent element. The data analysis device 50 is connected to the data acquisition unit 10, the display device 61 and the input device 62.

The analysis processing part 51 is provided with an extraction part 52 and a data processing part 53, as a functional constituent element. The analysis processing part 51 extracts a target pixel configuring an image of a cell such as a nerve cell which is to be analyzed from the moving image data acquired by the moving-image acquisition part 40. The analysis processing part 51 performs analysis processing on the luminance value data which is analysis data and which is provided in the target pixel.

The extraction part 52 includes a luminance-value-data acquisition part (luminance-value-data acquisition means) 52a, a luminance-value extraction part (luminance-value extraction means) 52b and a pixel extraction part (pixel extraction means) 52c. The extraction part 52 extracts a target pixel configuring an image of a cell such as a nerve cell on which analysis processing is to be actually performed, from a measurement region corresponding to the well 21. The target pixel is extracted on the basis of a feature value indicating a feature of a waveform of the luminance value data. Examples of the feature value include a peak value provided in the waveform of the luminance value data, a bottom value a change ratio during Ratio calculation, a frequency, a cycle, an interval of peak values, a rising speed, a falling speed and integration value. In the present embodiment, a case where the feature value is the peak value and the bottom value will be described. The extraction part 52 is connected to the data processing part 53. Further, the extraction part 52 is connected to the threshold-value recording part 54.

The threshold-value recording part 54 records a threshold value relating to various types of evaluation values used when the target pixel is extracted. Examples of the threshold value include a peak-value threshold value, an amplitude threshold value and a change-ratio threshold value. The threshold-value recording part 54 is configured so as to be referenced from the extraction part 52.

The luminance-value-data acquisition part 52a acquires the luminance value data from the moving image data input from the moving-image acquisition part 40. That is, the luminance-value-data acquisition part 52a acquires the luminance value data for each pixel in the measurement region of the moving image data input from the data acquisition unit 10. The luminance value data indicates a temporal alteration in the luminance value provided in the pixel. The luminance value data acquired in the luminance-value-data acquisition part 52a is output to the luminance-value extraction part 52b.

The luminance-value extraction part 52b extracts the peak value and the bottom value from the luminance value data of the pixel input from the luminance-value-data acquisition part 52a. The peak value and the bottom value are output to the pixel extraction part 52c.

The pixel extraction part 52c extracts the target pixel configuring an image of a nerve cell, on the basis of the peak value and the bottom value input from the luminance-value extraction part 52b. Information of the target pixel is output to the data processing part 53. A method of extracting a target pixel will be described in detail later.

The data processing part (data processing means) 53 includes a phase correction part (correction, means) 53a, a luminance-value-data processing part (processing means) 53b and a luminance-value-data identification part (identification means) 53c. The data processing part 53 refers to the target pixel extracted in the extraction part 52, uses, as the analysis data, the luminance value data provided in the target pixel, and performs the analysis processing on the target pixel configuring an image of a nerve cell. The data processing part 53 is connected to the extraction part 52. Further, the data processing part 53 is connected to the specimen-luminance-value-data recording part 55.

The phase correction part 53a corrects a timing at which, in the luminance value data provided in the extracted target pixel, the luminance value changes from the bottom value to the peak value in order to align the phase of the luminance value data for each pixel. The phase correction part 53a corrects the phase of each luminance value data on the basis of a rising time, a peak time, etc. The luminance value data corrected by the phase correction part 53a is output to the luminance-value-data processing part 53b.

The luminance-value-data processing part 53b calculates an average of the corrected luminance value data that is corrected in phase by the phase correction part 53a. An averaged luminance value data calculated by the luminance-value-data processing part 53b is output to the display device 61 or the luminance-value-data identification part 53c.

The luminance-value-data identification part 53c identifies an image configured by a target pixel. The identification is performed by using the averaged luminance value data calculated by the luminance-value-data processing part 53b and the specimen luminance value data recorded on the specimen-luminance-value-data recording part 55.

Figure 5:
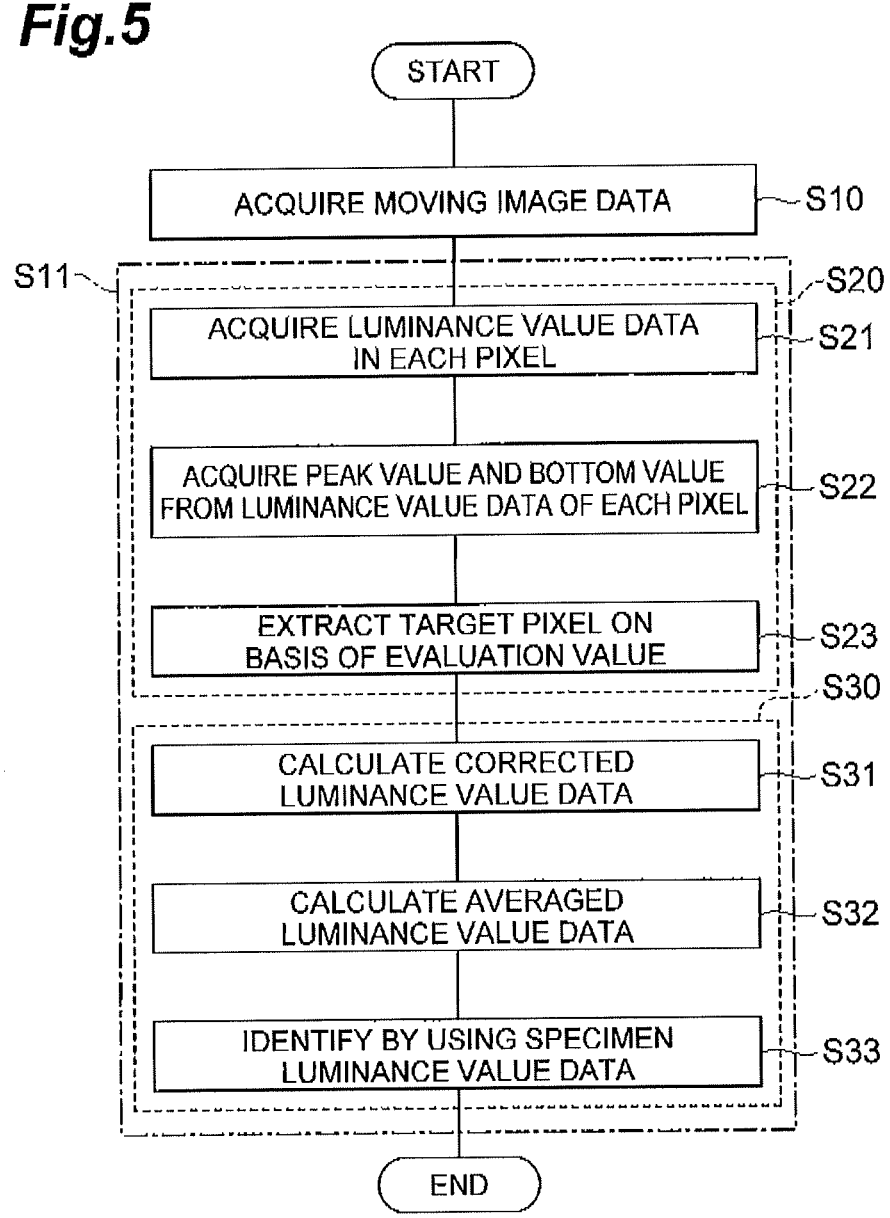
FIG. 5 is a diagram showing one embodiment of a light measurement method.

Next, the light measurement method executed by the light measurement device 1 will be described, and the light measurement method according to the present embodiment will be described in detail. Here, a step of extracting a target pixel configuring an image of a nerve cell from the moving image data will be described. FIG. 5 is a diagram for describing major steps of the light measurement method according to one embodiment.

Step S10 is executed by the moving-image acquisition part 40 of the data acquisition unit 10. In step S10, the moving image data of the two-dimensional light image is acquired (moving-image acquisition step). The two-dimensional light image is an image of the micro plate including the light from the sample S including the cell held inside the well 21 of the micro plate 20. In this case, the moving image data refers to a group of two-dimensional image data obtained by temporally altering the two-dimensional image data detected at predetermined time intervals. The moving image data enables the extraction of a temporal change in the luminance value of each pixel.

First, a two-dimensional image of the micro plate 20 is detected by the image pickup device 45 of the moving-image acquisition part 40 so as to acquire the moving image data. The micro plate 20 holds the sample S including a cell within the well 21. The moving image data is acquired only during a previously set time. The set time is a time while the luminance value changes from the bottom value to the peak value, the luminance value is then returned to the bottom value in the change in the luminance value. That is, the set time may be a time during which a waveform of at least one cycle can be confirmed, and for example, 10 seconds or more. Further, the set time may be set to be longer than the time during which the waveform of one cycle is confirmed, and may be a time during which a plurality of waveforms can be confirmed. The acquired moving image data is input to the data analysis device 50 from the data acquisition unit 10.

Step S11 is executed by the data analysis device 50. In step S11, the analysis processing is performed on the moving image data acquired in step S10 by the data acquisition unit 10 (analysis processing step). Step S11 includes a step of extracting the target pixel which is to be analyzed (extraction step), and a step of implementing the analysis processing on the target pixel (data processing step).

Step S20 is executed by the extraction part 52 of the data analysis device 50. At step S20, on the basis of the luminance value data in the pixel of the moving image data acquired in step S10, the target pixel which is to be a target of an analysis region is extracted. Step S20 includes a luminance-value-data acquisition step S21, a luminance-value extraction step S22 and a pixel extraction step S23. In luminance-value-data acquisition step S21, luminance value data in each pixel is acquired. In luminance-value extraction step S22, the peak value and the bottom value are acquired from the luminance value data of each pixel as one example of the characteristics of the luminance value data. In pixel extraction step S23, on the basis of the peak value and the bottom value, the target pixel is extracted.

Step S21 is executed by the luminance-value-data acquisition part 52a. In step S21, the luminance value data for each pixel is acquired.

Step S22 is executed by the luminance-value extraction part 52b. In step S22, the peak value and the bottom value are extracted from the luminance value data acquired in step S21. At least one peak value is extracted from a temporal alteration in the luminance value data in one pixel. Similarly, at least one bottom value is extracted from a temporal alteration in the luminance value data in one pixel.

Step S23 is executed by the pixel extraction part 52c. In step S23, on the basis of the peak value and the bottom value acquired in step S22, the target pixel is extracted. First, an evaluation value for evaluating a state of a change in the luminance value is calculated. For the evaluation value, either one of the amplitude of the luminance value or the change ratio (ratio value) of the luminance value is used. The peak value is an absolute value L of a peak appearing in the luminance value data. The bottom value is an absolute value B of a bottom appearing in the luminance value data. As the bottom value, luminance value data of a background acquired in advance may be used. The amplitude of the luminance value is a difference (L−B) between the peak value and the bottom value. The change ratio of the luminance value is a ratio (L/B) of the peak value relative to the bottom value.

As the evaluation value, only the amplitude of the luminance value may be used, and only the change ratio of the luminance value may be used. Further, as the evaluation value, both the amplitude of the luminance value and the change ratio of the luminance value may be used. When the amplitude of the luminance value and the change ratio of the luminance value are used as the evaluation value, it may be possible that the pixel is extracted by using the amplitude of the luminance value, and then, further extracted by using the change ratio of the luminance value from the extracted pixel. It may be possible that the pixel is extracted by using the change ratio of the luminance value, and then, further extracted by using the amplitude of the luminance value from the extracted pixel.

Further, in addition to the amplitude of the luminance value and the change ratio of the luminance value, a peak cycle, a peak count, a peak time, a rising time, a falling time and a peak amplitude range may be used as the evaluation value. The peak cycle refers to a cycle when a peak equal to or more than a threshold value is repeated. The peak count refers to the number of times that a peak equal to or more than a threshold value appears. The peak time refers to, for example, a time from a predetermined timing such as a timing at which a drug is administered until a peak is reached. The rising time refers to a time until the luminance value reaches the peak value from the bottom value. The falling time refers to a time until the luminance value returns from the peak value to the bottom value. The peak amplitude range refers to a time difference between the peak time in one pixel and the peak time in another pixel adjacent to the one pixel.

The above-described evaluation values can be used by combining with at least either one of the amplitude of the luminance value or the change ratio of the luminance value. It may be possible to select one of the peak cycle, the peak count, the peak time, the rising time, the falling time and the peak amplitude range to be used as the evaluation value in combination therewith, and it may be also possible to select a plurality of items to be used and combined as the evaluation value. When the pixel is extracted by using a plurality of evaluation values, the order that the evaluation values are applied is not particularly limited, and the evaluation values can be applied in a desired order.

In the extraction according to one embodiment, there is a case where a desired cell image is screened from the moving image data and a case where different types of cell images included in the moving image data are classified according to each type.

When the desired cell image is screened from the moving image data, it is possible to screen the desired cell image by using a plurality of evaluation values in combination, for example. When the luminance value data provided in the desired cell image can be specified by an amplitude of a predetermined luminance value and a predetermined peak time, for example, it is possible to screen the desired cell image from the moving image data by extracting the pixel by using these evaluation values.

When the different types of cell images included in the moving image data are classified according to each type, it is possible to classify different types of cell images according to each type by setting a plurality of threshold values to at least one evaluation value, for example. For example, as for the amplitude of the luminance value, threshold values, that is, X1 and X2, are set. The threshold value X1 is assumed to be a larger value than the threshold value X2. In this case, it is possible to classify into groups, that is, a group where the amplitude of the luminance value is equal to or more than X1, a group where the amplitude of the luminance value is equal to or more than X2 and less than X1, and a group where the amplitude of the luminance value is less than X2.

Step S30 is executed by the data processing part 53. In step S30, analysis processing is executed on the target pixel configuring an image of a nerve cell extracted in step S20. Step S30 includes a correction step S31, a processing step S32 and an identification step S33. In correction step S31, corrected luminance value data in which the phase of the luminance value data of the pixel in the analysis region is corrected is calculated. In processing step S32, on the basis of the corrected luminance value data, the averaged luminance value data is calculated. In identification step S33, by comparing the averaged luminance value data with the specimen luminance value data acquired in advance, the image configured by the target pixel is identified.

Step S31 is executed by the phase correction part 53a. In step S31, a timing at which the luminance value changes from the bottom value to the peak value is corrected. The temporal alteration in the luminance value radiated from the cell differs in how a stimulation is transmitted depending on a location of a cell and a drug administration, therefore, there is a case where a timing at which the reaction appears lags. For example, a timing at which the reaction appears in a pixel configuring an image of a nerve cell located away from the center of a stimulation lags behind a timing at which the reaction appears in a pixel configuring an image of a nerve cell located closer to the center of the stimulation. The timing lag is corrected by the phase correction part 53a by matching the timing at which the luminance value changes from the bottom value to the peak value among a plurality of pixels. This enables an improvement in the measurement sensitivity. It should be noted that if the timing lag is within a time range set in advance, step S31 may be omitted.

Step S32 is executed by the luminance-value-data processing part 53b. In step S32, on the basis of the corrected luminance value data, averaging processing is performed on the luminance value data. In the averaging process, the averaged luminance value data is calculated. The averaged luminance value data refers to data obtained by averaging the luminance value data of the extracted target pixel for each two-dimensional image data. This enables calculation of an average luminance of the light emitted from a cell at a specific time. The averaged luminance value data is calculated by using the corrected luminance value data corrected in phase in step S31, and it is thus possible to improve the measurement sensitivity. Further, when there are a plurality of nerve cells in the well 21, calculation may be performed for the averaged luminance data obtained by averaging the luminance value data of the target pixel for each region of the nerve cell configured by the target pixel.

Step S33 is executed by the luminance-value-data identification part 53*c*. In step S33, the types of the image configured by the target pixel are identified by using the specimen luminance value data. The identification processing is executed by comparing the averaged luminance value data calculated in step S32 and the specimen luminance value data that is acquired and recorded in advance on the specimen-luminance-value-data recording part 55. For example, when the averaged luminance value data is included within a tolerance set to the specimen luminance value data, the cell image having the averaged luminance value data is identified as a specific cell represented by the specimen luminance value data. Further, in step S33, the specimen luminance value data may be identified by using a specifiable evaluation value.

A light measurement program causing a computer to operate as the data analysis device 50 will be described below.

A light measurement program according to one embodiment is provided by being stored in a recording medium. Examples of the recording medium include a recording medium such as a floppy (registered trademark) disk, a CD-ROM, a DVD or a ROM, or a semiconductor memory.

Figure 6:
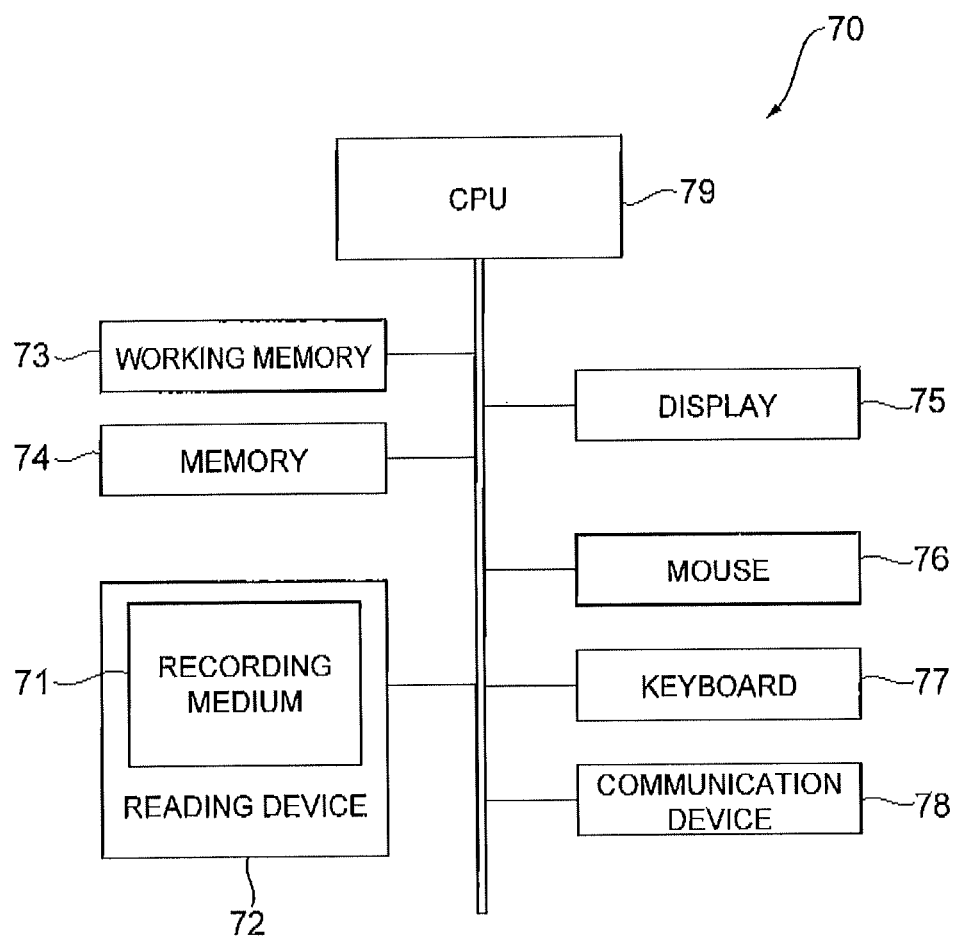
FIG. 6 is a diagram showing a hardware configuration of a computer for executing a program recorded on a recording medium.
Figure 7:
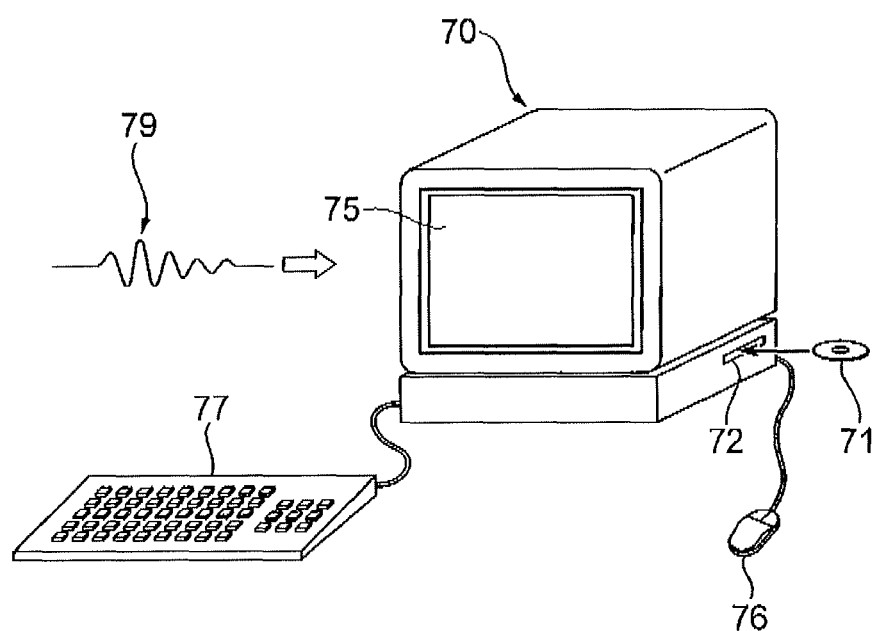
FIG. 7 is a diagram showing a computer for executing a program recorded on a recording medium.

FIG. 6 is a diagram showing a hardware configuration of a computer for executing a program recorded on a recording medium. FIG. 7 is a diagram of a computer for executing a program recorded on a recording medium. The computer includes various types of data processing devices that are provided with a CPU and that are for performing processing or control by software, such as a server device and a personal computer.

As shown in FIG. 6, a computer 70 is provided with a reading device 72 such as a floppy (registered trademark) disk drive device, a CD-ROM drive device and a DVD drive device, a working memory (RAM) 73 in which an operating system permanently resides, a memory 74 for storing a program stored on a recording medium 71, a display device 75 such as a display, a mouse 76 and a keyboard 77 that are input devices, a communication device 78 for transmitting and receiving data, etc., and a CPU 79 for controlling the execution of a program. The computer 70 allows access from the reading device 72 to the light measurement program which is stored in the recording medium 71 upon insertion of the reading medium 72 into the recording medium 72, and becomes operable by the light measurement program as the light measurement device 1 according to the present embodiment.

As shown in FIG. 7, the light measurement program may be provided as a computer data signal 79 superimposed on a carrier wave via a network. In this case, the computer 70 stores the light measurement program received by the communication device 78 into the memory 74, and can execute the light measurement program.

According to the light measurement device 1, the light measurement method, and the light measurement program, the two-dimensional light image of the micro plate 20 is detected, and the two-dimensional moving image data is acquired (S10). The two-dimensional light image includes a cell held within the well 21 of the micro plate 20. Next, the luminance value data indicating the temporal alteration in the luminance value in a plurality of pixels configuring the moving image data is acquired (S21). Then, the peak value and the bottom value of the luminance value are acquired from the luminance value data (S22). On the basis of either one of the amplitude of the luminance value obtained from the difference between the peak value and the bottom value or the change ratio of the luminance value obtained by a ratio of the peak value relative to the bottom value, the target pixel configuring the image of the nerve cell is extracted from a plurality of pixels (S23). Thus, the amplitude of the luminance value and the change ratio of the luminance value based on the temporal alteration in the luminance value are used, therefore, it is possible to divide the pixel configuring the image of the nerve cell from which light having the luminance value that temporally alters is emitted.

Further, in the light measurement device 1, the evaluation value further includes: a peak cycle; a peak count; a peak time defined by a time until the luminance value reaches from a predetermined timing to a peak; a rising time defined by a time until the luminance value reaches the peak value from the bottom value; a falling time defined by a time until the luminance value returns from the peak value to the bottom value; and a peak amplitude range that is a difference between the peak time in one pixel and the peak time in another pixel adjacent to the one pixel. The pixel extraction part 52*c* extracts the target pixel on the basis of at least one of the peak cycle, the peak count, the peak time, the rising time, the falling time and the peak amplitude range. According thereto, as the evaluation value representing a temporal alteration in the luminance value, the peak cycle, the peak count, the peak time, the rising time, the falling time and the peak amplitude range are used as the parameter for extracting the target pixel configuring an image of a nerve cell so as to extract the target pixel (S23). Therefore, it is possible to minutely distinguish the characteristics of the temporal alteration in the luminance value, and it is thus possible to accurately divide the target pixel configuring the image of the nerve cell.

When the peak cycle is used as the evaluation value, it becomes possible to make a classification based on an oscillation cycle of a cell that oscillates (for example, changes in a Ca ion of a nerve and a muscle), or a classification based on a cycle change after a medicinal effect. Further, when the peak count is used as the evaluation value, it becomes possible to make a classification based on an oscillation count of a cell or a classification based on an oscillation count after a medicinal effect. Further, when the rising time is used as the evaluation value, it becomes possible to make a classification based on an arrival time (speed) to the peak value as an effect of a medicinal effect response. Further, when the falling time is used as the evaluation value, it becomes possible to classify a cell that is slow in recovery due to a damage after a medicinal effect.

In the light measurement device 1, the analysis processing part 51 may further include: the phase correction part 53*a* for calculating the corrected luminance value data by correcting a phase deviation between a plurality of luminance value data after extracting the target pixel; and a luminance-value-data processing part 53*b* for calculating the averaged luminance value data by averaging, per time, a plurality of corrected luminance value data. According thereto, the corrected luminance value data is calculated by correcting the luminance value data of the pixel extracted by the pixel extraction part 52*c* (S31). Then, a plurality of corrected luminance value data are averaged so as to calculate the averaged luminance value data (S32). Therefore, it is possible to perform analysis processing in which measurement sensitivity to the light emitted from the cell is improved.

In the light measurement device 1, the analysis processing part 51 may further include the luminance-value-data identification part 53c for identifying the image configured by the target pixel by comparing the averaged luminance value data and the specimen luminance value data acquired in advance. According thereto, it is possible to distinguish a type of an image configured by a desired cell image.

EXAMPLE 1

Figure 8:
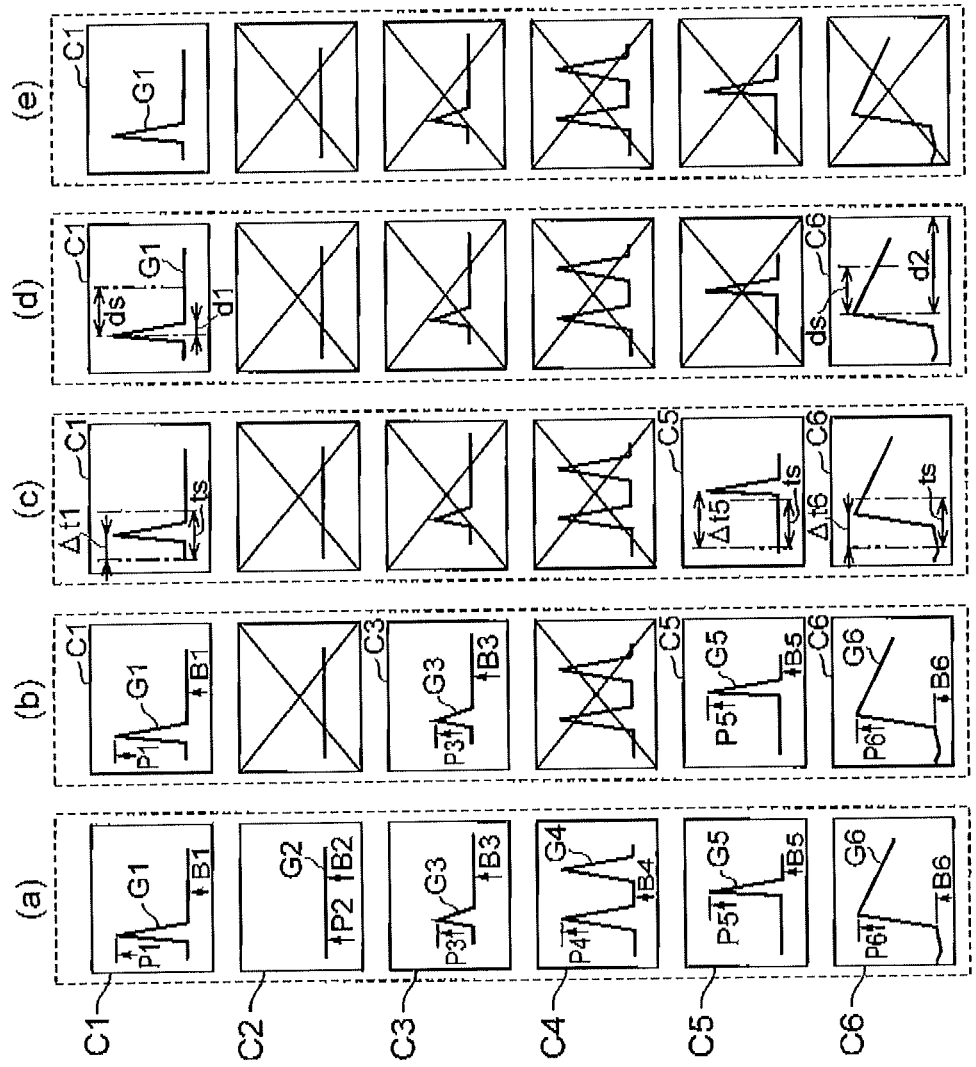
FIG. 8 is a diagram for describing an example of a light measurement method.

A step of screening a pixel having predetermined luminance value data from a plurality of pixels configuring the moving image data will be specifically described. FIG. 8(a) shows results obtained when step S21 (luminance value data acquisition step) is executed. Each of a plurality of pixels C1 to C6 has luminance value data shown in graphs G1 to G6. In the Example 1, processing for dividing the pixel C1 having the luminance value data G1 is employed as an example for a description.

For the evaluation value for dividing the pixel C1, the peak count, the amplitude of the luminance value, the peak time and the falling time are used. A threshold value of the peak count is equal to or more than 1 and less than 2. A threshold value of the amplitude of the luminance value is equal to or more than a predetermined amplitude threshold value. A threshold value of the peak time is equal to or less than ts. A threshold value of the falling time is equal to or less than ds.

Next, peak values P1 to P6 and bottom values B1 to B6 are acquired from each of luminance value data G1 to G6 (S22). Next, the pixel is extracted by applying the peak count as the evaluation value. A threshold value used in this case is 'equal to or more than 1 and less than 2.' In the luminance value data G1 to G6, the peak count of the luminance value data G1, G3, G5 and G6 is '1,' the peak count of the luminance value data G2 is '0,' and the peak count of the luminance value data G4 is '2.' Thus, from among the luminance value data G1 to G6, items that satisfy the threshold value of 'equal to or more than 1 and less than 2' are the luminance value data G1, G3, G5 and G6, and, as shown in FIG. 8(b), the pixels C1, C3, C5 and C6 are therefore extracted.

Next, the pixel is extracted by applying the amplitude of the luminance value as the evaluation value. The peak values P1, P3, P5 and P6, and the bottom values B1, B3, B5 and B6 provided in the extracted pixels C1, C3, C5 and C6 are used to calculate the amplitude of the luminance value. From among the amplitude of the luminance value calculated from each of the luminance value data G1, G3, G5 and G6, when items that satisfy the threshold value are the luminance value data G1, G5 and G6, the pixels C1, C5 and C6 are extracted, as shown in FIG. 8(c).

Next, the pixel is extracted by applying the peak time as the evaluation value. First, peak times Δt1, Δt5 and Δt6 provided in the extracted pixels C1, C5 and C6 are acquired. A threshold value used in this case is 'equal to or less than ts.' Thus, from among the luminance value data G1, G5 and G6, items that satisfy the threshold value are the luminance value data G1 and G6. Therefore, as shown in FIG. 8(d), the pixels C1 and C6 are extracted as the target pixel.

Next, the pixel is extracted by applying the falling time as the evaluation value. First, falling times d1 and d2 provided in the extracted pixels C1 and C6 are acquired. A threshold value used in this case is 'equal to or less than ds.' Therefore, from among the luminance value data G1 and G6, an item that satisfies the threshold value is the luminance value data G1. Therefore, as shown in FIG. 8(e), the pixel C1 is extracted as the pixel configuring an image of a predetermined cell. Thus, from the moving image data, a plurality of pixels having the luminance value data G1 are divided.

Figure 10:
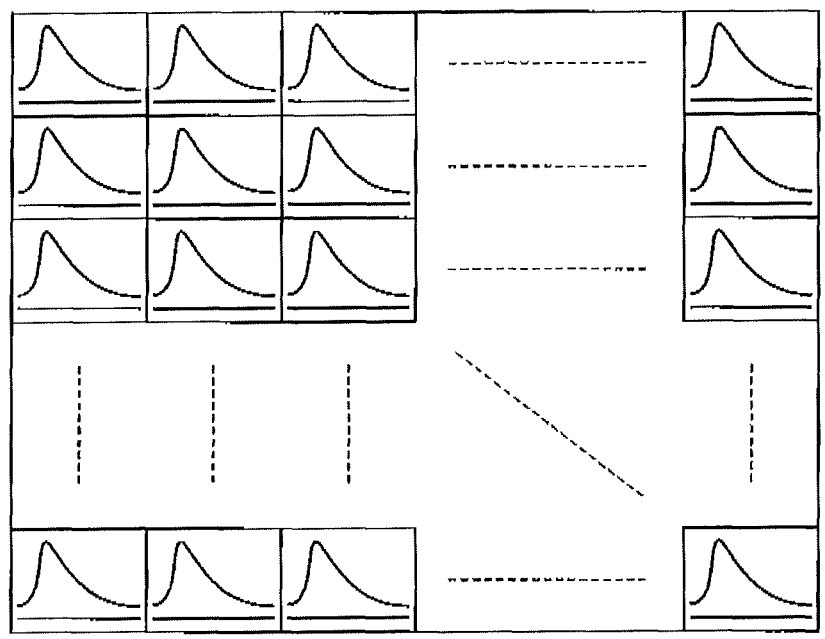
FIG. 10 is a diagram showing one example of a display of analysis results.

The method according to the above-described Example 1 can be used, for example, for an oscillation analysis of a cell by a calcium ion. First, the luminance value data of all the pixels configuring an image of the well 21 are acquired. Second, from the luminance value data, a pixel having predetermined luminance value data is extracted. Next, the averaging processing is performed on the extracted luminance value data. Then, results obtained by the averaging processing are displayed on the display device 61 for each well 21. For example, as shown in FIG. 10, a screen is divided into a plurality of two-dimensionally arrayed display regions (in FIG. 10, 8×12=96 display regions), and the averaged luminance value data in the well 21 corresponding to each of the display regions is displayed.

The method according to the above-described Example 1 can be used for identifying a cell image, for example. First, a predetermined cell within the well 21 is stained. Second, a light wavelength to be observed in the moving-image acquisition part 40 is switched, and the moving image data is acquired. Next, the luminance value data of all the pixels configuring the image of the well 21 are acquired. Then, by using a method such as that in the above-described Example 1, a pixel configuring an image of a cell stained by predetermined staining reagent is extracted. Further, the averaging processing is performed on the luminance value data of the extracted pixel. Then, by using standard luminance value data, the luminance value data subjected to the averaging processing is identified. This enables the identification of the cell image.

EXAMPLE 2

Figure 9:
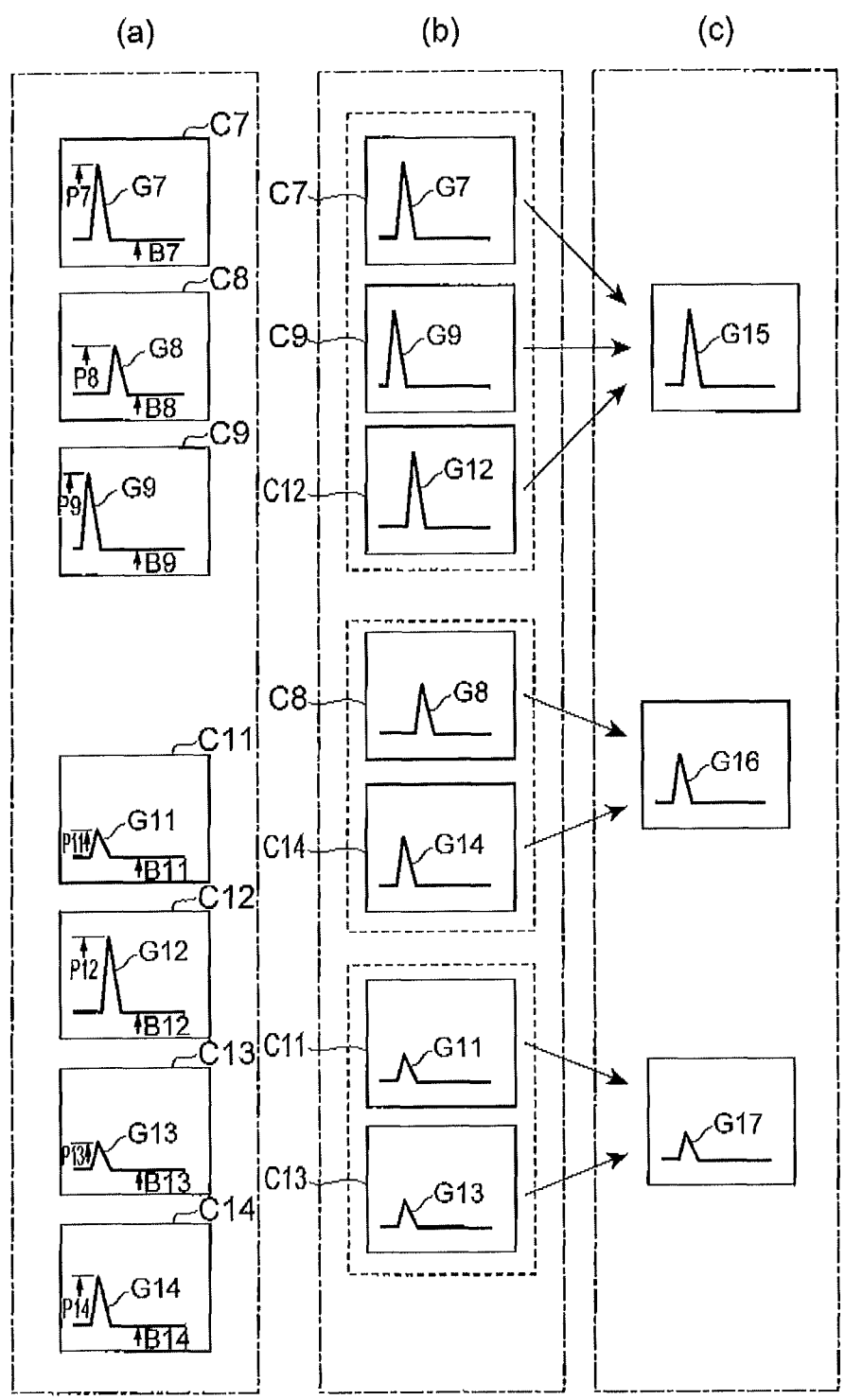
FIG. 9 is a diagram for describing another example of the light measurement method.

A step of dividing a plurality of pixels configuring the moving image data according to a predetermined classification condition and displaying the classified luminance value data will be specifically described. FIG. 9(a) shows results obtained by executing step S21 (luminance value data acquisition step) after executing step S10 (moving-image acquisition step). Each of a plurality of pixels C7 to C14 has the luminance value data shown in graphs G7 to G14. In the Example 2, the process of classifying a plurality of pixels C7 to C14 for each luminance value data that satisfies a predetermined condition will be described. In this case, by using the amplitude of the luminance value as the evaluation value, a plurality of pixels are classified into three groups. Therefore, two amplitude threshold values v0 and v1 are used. The amplitude threshold value v1 is assumed to be larger than the amplitude threshold value v0. According to this, it is possible to divide pixels into groups, that is, a group of pixels where the amplitude of the luminance value is equal to or more than v1, a group of pixels where the amplitude of the luminance value is less than v1 and equal to or more than v0, and a group of pixels where the amplitude of the luminance value is less than v0.

First, from each of the luminance value data G7 to G14, peak values P7 to P14 and bottom values B7 to B14 are acquired. Then, from the peak values P7 to P14 and the bottom values B7 to B14, the amplitude of the luminance value is calculated.

Next, by using the calculated amplitude of the luminance value and the two amplitude threshold values, a plurality of pixels are classified. As a result, as shown in FIG. 9(b), pixels C7, C9 and C12 are extracted as the pixel where the amplitude of the luminance value is equal to or more than v1. Further, C8 and C14 are extracted as the pixel where the amplitude of the luminance value is less than v1 and equal to or more than v0. Moreover, C11 and C13 are extracted as the pixel where the amplitude of the luminance value is less than v0. Thus, it is possible to divide a plurality of pixels C7 to C14 into the three groups.

Next, the luminance value data belonging to the same group is corrected in phase among the pixels C7, C9 and C12, in step S31 (correction step). Similarly, the phase is corrected between the pixels C8 and C14. Further, the phase is corrected between the pixels C11 and C13. Then, as shown in FIG. 9(c), in step S32 (data processing step), the corrected luminance value data are combined. Thereafter, the corrected luminance value data G7, G9 and G12 are combined, and the averaged luminance value data G15 is calculated. The corrected luminance value data G8 and G14 are combined, and the averaged luminance value data G16 is calculated. The corrected luminance value data G11 and G13 are combined, and the averaged luminance value data G17 is calculated. Then, the combined luminance value data G5, G16 and G17 are displayed on the display device 61. It should be noted that in the above-described Example 2, after the plurality of pixels C7 to C14 are divided into the three groups, the phase correction is performed; however, the phase correction may be implemented before being divided into the three groups.

As in the above-described Example 2, a method of classifying a plurality of pixels may be used for a function analysis, of a nerve cell, etc., using a calcium ion, for example. First, the luminance value data of all the pixels configuring an image of the well 21 are acquired. Second, the luminance value data are classified by using a predetermined classification condition. Next, averaging processing is performed on the luminance value data classified into the same group. Then, results obtained by the averaging processing are displayed on the display device 61 independently by each extraction condition.

As described above, one embodiment of the light measurement device, the light measurement method, and the light measurement program has been described; however, the light measurement device, the light measurement method, and the light measurement program are not limited to the above embodiment. For example, in the above-described embodiment, the nerve cell has been described as an example of a predetermined cell; however, it is possible to use a cell different from a nerve cell as the predetermined cell. For example, an epithelial cell, a smooth muscle cell, a skeletal muscle cell, a vascular endothelial cell, a blood cell, an osteoblast cell, an osteoclast cell, an organ cell, and a cell line may be used.

INDUSTRIAL APPLICABILITY

According to the light measurement device, the light measurement method, and the light measurement program, it is possible to divide a pixel configuring an image of a cell in which a luminance value temporally alters in an image including light emitted from a sample including a nerve cell, etc.

REFERENCE SIGNS LIST

1 . . . light measurement device, 20 . . . micro plate, 21 . . . well, 40 . . . moving-image acquisition part, 50 . . . data processing device, 51 . . . analysis processing part, 52a . . . luminance-value-data acquisition part, 52b . . . luminance-value extraction part, 52c . . . pixel extraction part, S . . . sample.

The invention claimed is:

1. A light measurement apparatus for measuring light from a sample including a cell, comprising;
an analysis processing means configured to;
acquire luminance-value data from a pixel of an image of the sample over time, wherein the image of the sample comprises an image of the cell, the pixel is associated with a location within the sample, and the acquired luminance-value data indicates a temporal alteration in light detected at the location of the sample;
evaluate the temporal alteration in the luminance-value data of the pixel based on a temporal light emission characteristic of the cell, to determine a presence of the cell at the location of the sample;
identify the pixel associated with the luminance-value data as a target pixel, wherein the target pixel forms at least part of the image of the cell and wherein the image of the sample comprises pixels including the target pixel;
extract at least one additional target pixel from the pixels of the image of the sample, as forming at least part of the image of the cell, to obtain together with the target pixel a group of target pixels being associated with a plurality of luminance-value data, wherein the plurality of luminance-value data comprises a phase deviation representing a timing lag between the luminance value data acquired from the target pixel and the luminance value data acquired from the at least one additional target pixel;
correct the phase deviation between the plurality of luminance value data by calculating a plurality of corrected-luminance-value data in which the phase deviation in the plurality of luminance-value data has been corrected;
calculate averaged-luminance-value data that is an average of the plurality of corrected luminance value data;
wherein the luminance-value data comprises a luminance value of the pixel as a function of time, and wherein the analysis processing means is further configured to evaluate the temporal alteration by: extracting a peak value and a bottom value of the luminance-value from the luminance-value data associated with the pixel; and calculating an evaluation value on the basis of the peak value and the bottom value; and comparing the evaluation value with at least one threshold associated with the temporal light emission characteristic of the cell, to determine the presence of the cell at the location of the sample, associated with the pixel; and
wherein, analysis processing means is configured to calculate, as the evaluation value at least one of: an amplitude of the luminance value obtained from a difference between the peak value and the bottom value; and a change ratio of the luminance value obtained from a ratio of the peak value relative to the bottom value.

2. The light measurement apparatus according to claim 1, further comprising a non-transitory recording medium having recorded thereon specimen-luminance-value data associated with a cell type, wherein the analysis processing means is further configured to: compare the averaged-luminance-value data and the specimen-luminance-value data; and identify the cell type in association with the cell, when the averaged-luminance-value data associated with the group of target pixels matches the specimen-luminance-value data.

3. The light measurement apparatus according to claim 1, wherein analysis processing means is further configured to calculate, as the evaluation value, at least one of: a peak cycle; a peak count; a peak time defined by a time until the luminance value reaches from a predetermined timing to a peak; a rising time defined by a time until the luminance value reaches the peak value from the bottom value; a falling time defined by a time until the luminance value returns from the peak value to the bottom value; and a peak amplitude range that is a difference between the peak time associated with the pixel and a peak time of luminance-value data of another pixel adjacent to the pixel.

4. The light measurement apparatus according to claim 1, wherein the light measurement apparatus is immobile relative to the sample when acquiring the luminance-value data.

5. The light measurement apparatus according to claim 1, further comprising: an image pickup device configured to acquire the image of the sample by converting light detected from the sample into a luminance value at each of the pixels, a plurality of times during a time period; and a holding part for holding the sample at a fixed measurement position relative to the image pickup device for an entire duration of the time period during which the image of the sample is acquired by the image pickup device.

6. The light measurement apparatus according to claim 1, wherein the plurality of luminance-value data comprise bottom values that change toward peak values at respective change timings, and wherein correcting the phase deviation comprises reducing the phase deviation in order to substantially match together the change timings of the plurality of luminance-value data.

7. A light measurement method of measuring light from a sample including a cell, comprising:
acquiring luminance-value data from a pixel of an image of the sample over time, wherein the image of the sample comprises an image of the cell, the pixel is associated with a location within the sample, and the luminance-value data indicates a temporal alteration in light detected at the location of the sample;
evaluating the temporal alteration in the luminance-value data of the pixel based on a temporal light emission characteristic of the cell, to determine a presence of the cell at the location of the sample;
identifying the pixel associated with the luminance-value data as a target pixel, wherein the target pixel forms at least part of the image of the cell and wherein the image of the sample comprises pixels including the target pixel;
extracting at least one additional target pixel from the pixels of the image of the sample, as forming at least part of the image of the cell, to obtain together with the target pixel a group of target pixels being associated with a plurality of luminance-value data, wherein the plurality of luminance-value data comprises a phase deviation representing a timing lag between the luminance value data acquired from the target pixel and the luminance value data acquired from the at least one additional target pixel;
correcting the phase deviation between the plurality of luminance value data by calculating a plurality of corrected-luminance-value data in which the phase deviation in the plurality of luminance-value data has been corrected;
calculating averaged-luminance-value data that is an average of the plurality of corrected luminance value data;
wherein the luminance-value data associated with the pixel comprises a luminance value as a function of time, and wherein the evaluating step further comprises: extracting a peak value and a bottom value of the luminance value from the luminance-value data; calculating an evaluation value on basis of the peak value and the bottom value; and comparing the evaluation value with at least one threshold associated with the temporal light emission characteristic of the cell, to determine the presence of the cell at the location of the sample, associated with the pixel; and
wherein the calculating step calculates, as the evaluation value, at least one of: an amplitude of the luminance value obtained from a difference between the peak value and the bottom value; and a change ratio of the luminance value obtained from a ratio of the peak value relative to the bottom value.

8. The light measurement method according to claim 7, wherein the calculating step calculates, as the evaluation value, at least one of: a peak cycle; a peak count; a peak time defined by a time until the luminance value reaches from a predetermined timing to a peak; a rising time defined by a time until the luminance value reaches the peak value from the bottom value; a falling time defined by a time until the luminance value returns from the peak value to the bottom value; and a peak amplitude range that is a difference between the peak time associated with the pixel and a peak time of luminance-value data of another pixel adjacent to the pixel.

9. The light measurement method according to claim 7, wherein specimen-luminance-value data of a cell type is recorded, the method further comprising: comparing the luminance-value data of the target pixel and the specimen-luminance-value data; and identifying the cell type in association with the image of the cell, when the luminance-value data of the target pixel matches the specimen-luminance-value data.

10. The light measurement method according to claim 7, wherein specimen-luminance-value data is recorded in association with a cell type, the method further comprising: acquiring luminance-value data for each of the pixels of the image of the sample, wherein extracting the at least one additional target pixel is based on the luminance-value data of the pixels; comparing the averaged-luminance-value data associated with the group of target pixels and the specimen-luminance-value data; and identifying the cell type in association with the image of the cell, when the luminance-value data associated with the group of target pixels matches the specimen-luminance-value data.

11. The light measurement method according to claim 10, further comprising classifying the pixels of the image of the sample into the group of target pixels based on an amplitude of a luminance value over time of the luminance-value data associated with the group of pixels.

12. The light measurement method according to claim 7, further comprising acquiring the image of the sample by converting light detected from the sample into a luminance value at each of the pixels, a plurality of times during a time period.

13. The light measurement method according to claim 12, wherein the image of the sample is acquired by an image pickup device and the sample is held at a fixed measurement position relative to the image pickup device for an entire duration of the time period during which the image of the sample is acquired.

14. The light measurement method according to claim 7, wherein the plurality of luminance-value data comprise bottom values that change toward peak values at respective change timings, and wherein correcting the phase deviation comprises reducing the phase deviation in order to substantially match together the change timings of the plurality of luminance-value data.

15. A non-transitory computer readable medium having stored thereon one or more sequences of instructions for causing one or more processors to perform the steps for measuring light from a sample including a cell, the steps comprising;
   acquiring luminance-value data from a pixel of an image of the sample over time, wherein the image of the sample comprises an image of the cell, the pixel is associated with a location within the sample, and the luminance-value data indicates a temporal alteration in light detected at the location of the sample;
   evaluating the temporal alteration in the luminance-value data of the pixel based on a temporal light emission characteristic of the cell, to determine a presence of the cell at the location of the sample;
   identifying the pixel associated with the luminance-value data as a target pixel, wherein the target pixel forms at least part of the image of the cell and wherein the image of the sample comprises pixels including the target pixel;
   extracting at least one additional target pixel from the pixels of the image of the sample, as forming at least part of the image of the cell, to obtain together with the target pixel a group of target pixels being associated with a plurality of luminance-value data, wherein the plurality of luminance-value data comprises a phase deviation representing a timing lag between the luminance value data acquired from the target pixel and the luminance value data acquired from the at least one additional target pixel;
   correcting the phase deviation between the plurality of luminance value data by calculating a plurality of corrected-luminance-value data in which the phase deviation in the plurality of luminance-value data has been corrected;
   calculating averaged-luminance-value data that is an average of the plurality of corrected luminance value data;
   wherein the luminance-value data associated with the pixel comprises a luminance value as a function of time, and wherein the evaluating step further comprises: extracting a peak value and a bottom value of the luminance value from the luminance-value data; calculating an evaluation value on basis of the peak value and the bottom value; and comparing the evaluation value with at least one threshold associated with the temporal light emission characteristic of the cell, to determine the presence of the cell at the location of the sample, associated with the pixel; and
   wherein the calculating step calculates, as the evaluation value, at least one of: an amplitude of the luminance value obtained from a difference between the peak value and the bottom value; and a change ratio of the luminance value obtained from a ratio of the peak value relative to the bottom value.

16. The non-transitory computer readable medium according to claim 15, wherein the luminance-value data was acquired while holding the sample at a measurement position.

17. The non-transitory computer readable medium according to claim 15, further storing specimen-luminance-value data associated with a cell type, and wherein the one or more sequences of instructions stored thereon are configured to cause the one or more processors to further perform the steps of; comparing the luminance-value data of the target pixel and the specimen-luminance-value data; and identifying the cell type in association with the image of the cell, when the luminance-value data of the target pixel matches the specimen-luminance-value data.

18. The non-transitory computer readable medium according to claim 15, wherein the plurality of luminance-value data comprise bottom values that change toward peak values at respective change timings, and wherein correcting the phase deviation comprises reducing the phase deviation in order to substantially match together the change timings of the plurality of luminance-value data.

* * * * *